United States Patent [19]

Kawaguchi et al.

[11] Patent Number: 4,820,649

[45] Date of Patent: Apr. 11, 1989

[54] METHOD AND KIT HAVING LAYERED DEVICE FOR DETECTING BIOLOGICAL COMPONENT BY INTERFERENCE COLOR

[75] Inventors: Takeyuki Kawaguchi, Hachioji; Takashi Shiro, Hino, both of Japan

[73] Assignee: Teijin Limited, Osaka, Japan

[21] Appl. No.: 99,906

[22] Filed: Sep. 22, 1987

[51] Int. Cl.$^4$ .................. G01N 33/53; G01N 33/553
[52] U.S. Cl. ..................................... 436/501; 422/57; 436/170; 436/518; 436/525; 436/805; 436/808
[58] Field of Search ............... 436/525, 805, 501, 518, 436/808, 170; 422/57

[56] References Cited

U.S. PATENT DOCUMENTS

| | | | |
|---|---|---|---|
| 3,926,564 | 12/1975 | Giaever | 436/805 X |
| 3,960,488 | 6/1976 | Giaever | 436/805 X |
| 4,054,646 | 10/1977 | Giaever | 436/805 X |
| 4,090,849 | 5/1978 | Healy | 436/805 X |
| 4,092,116 | 5/1978 | Giaever | 436/805 X |
| 4,313,734 | 2/1982 | Leuvering | 436/525 |
| 4,446,238 | 5/1984 | De Mey | 436/805 X |
| 4,508,832 | 4/1985 | Carter | 436/805 X |
| 4,558,012 | 12/1985 | Nygren | 436/501 |

Primary Examiner—Sidney Marantz
Attorney, Agent, or Firm—Wenderoth, Lind & Ponack

[57] ABSTRACT

A method for detecting a component of a biological system, which comprises contacting a biological component detecting device composed of a light reflecting substrate (I) substantially free from diffused reflection, a light interference layer (II) formed on the substrate (I), and a layer (III) of a substance for detecting said biological component provided at least in a region on the layer (II), with a solution presumed to contain the biological component to be detected, then forming a light-transmitting reflecting layer (IV) on its surface, and thereafter detecting the color of light interference or the brightness of the reflected light on the surface of the device.

28 Claims, 2 Drawing Sheets

METHOD AND KIT HAVING LAYERED DEVICE FOR DETECTING BIOLOGICAL COMPONENT BY INTERFERENCE COLOR

BACKGROUND OF THE INVENTION

This invention relates to a very simple and convenient immunological detecting method for detecting a component of a biological system, above all for immunological diagnosis, and to a device for immunological detection. More specifically, this invention relates to a method and a device for detecting an antigen or an antibody protein on the basis of an antigen-antibody reaction on a reflecting substrate.

Immunological diagnosis has been performed by utilizing an antigen-antibody reaction which is a very specific biochemical reaction. Radioimmunoassay (RIA), enzyme immunoassay (EIA), fluorescent immunoassay (FIA) and latex agglutination settling analysis (LSA), for example, are known and used in practice as specific methods of immunological diagnosis. These methods still have technical problems to be solved. RIA has very high detection sensitivity, but requires special facilities for handling radioactive elements. EIA requires a long period of time (usually several hours to one day) for the completion of detection. FIA does not have sufficient detection sensitivity. LSA cannot avoid a non-specific agglutination reaction, and has low reliability in detecting trace components.

On the other hand, an ellipsometric method was proposed in which an increase in the thickness of a protein layer which occurs with the progress of an antigen-antibody reaction on a solid substrate is detected by using elliptic polarized light (British Pat. No. 1,479,661). This method also requires an expensive device and much expertise is required for measuring the protein film thickness. There has also been proposed a method of detecting an antigen-antibody reaction simply with the unaided eye without using such an expensive device. For example, there is a method which comprises adsorbing and fixing an antibody (or an antigen) on and to the surface of gold particles deposited on a solid substrate, and visually observing changes in the color of the reflected light which occur as a result of an increase in the thickness of a layer of an immobilized antibody (or antigen) by an antigen-antibody reaction (U.S. Pat. No. 3,979,184). According to this method, the color of the complex of gold and the protein film on the solid substrate certainly changes with the antigen/antibody reaction. Since, however, the change is only slight from brown to dark brown and very obscure, the evaluation of the antigen-antibody reaction may possibly depend greatly upon the expertise of the testing personnel.

When an antigen or antibody is fixed to a dielectric layer formed on a highly light reflecting substrate such as a metallic chromium or tantalum substrate and an antigen-antibody reaction is carried out on its surface as shown, for example, by Langmuir and Blodgett, Physical Review, vol. 51, pages 964–978 (1937) or Vroman, Thromb. Diath. Haemorrhag., vol. 10, 455–493 (1964), the difference in refractive index between antigen or antibody and the air is very small and the reflectance on the surface of the antigen or antibody is as low as 5% at an incidence angle of 0° to 60°. On the other hand, the proportion of light reflected from the metallic substrate and coming back to the surface of the protein is higher than 50%. Accordingly, it is difficult to detect the interference color on the surface of the device. To discriminate this interference color with good efficiency, it is necessary to adjust the angle of reflection of light on the surface of the device to at least 60° to 70°, and it is difficult to detect with the unaided eye. Another proposal for solving this problem (U.S. Pat. No. 4,558,012) states that light interference occurs efficiently by providing two types of dielectric layers on a non-metallic substrate which does not so much reflect light, and making the amount of light reflected from the surface of the substrate nearly equal to that of light reflected from the surface of the dielectric layers. However, substrates meeting such conditions are limited to those which are colored or have high light transmitting property, and those having a high reflectance cannot be used. The colored substrates affect the interference color on the surface of the device and make the detection difficult. With the substrates having a high light transmittance, the color of the device becomes dark and light interference which gives a brilliant visible light color does not easily occur. If a substrate having a relatively high surface reflectance of 60 to 90% is used, it is essential to provide a plurality of dielectric layers having different refractive indices, and the process of building the device becomes complex.

SUMMARY OF THE INVENTION

The present inventors have made extensive investigations in order to develop a device for detecting a component of a biological system, which is free from the aforesaid problems of the prior art and permits easy and highly sensitive detection of the biological component with the unaided eyed. These investigations have now led to the discovery that if a thin film of fine metallic particles is provided on the surface of the device after reacting a detecting substance with a substance to be detected, optionally after the surface is subjected to a contrast enhancement treatment, the amount of light reflected from the surface of the substrate is balanced with the amount of the light reflected from the surface of the device within ranges where these amounts are large.

DETAILED DESCRIPTION OF THE INVENTION

According to this invention, there is provided a method for detecting a component of a biological system, which comprises (i) contacting a device for the detection of a biological component composed of a light reflecting substrate (I) substantially free from diffused reflection, a light interference layer (II) formed on the substrate (I), and a layer (III) of a substance for detecting said biological component provided at least in a region on the layer (II), with a solution presumed to contain the biological component to be detected, (ii)

then forming a light-transmitting reflecting layer (IV) on it, optionally after subjecting it to a contrast enhancement treatment, (iii) irradiating light onto it, preferably at an incidence angle of 0 to 50 degrees, and (iv) detecting the color of light interference or the brightness of the reflected light on the surface of the device.

Figure 1:
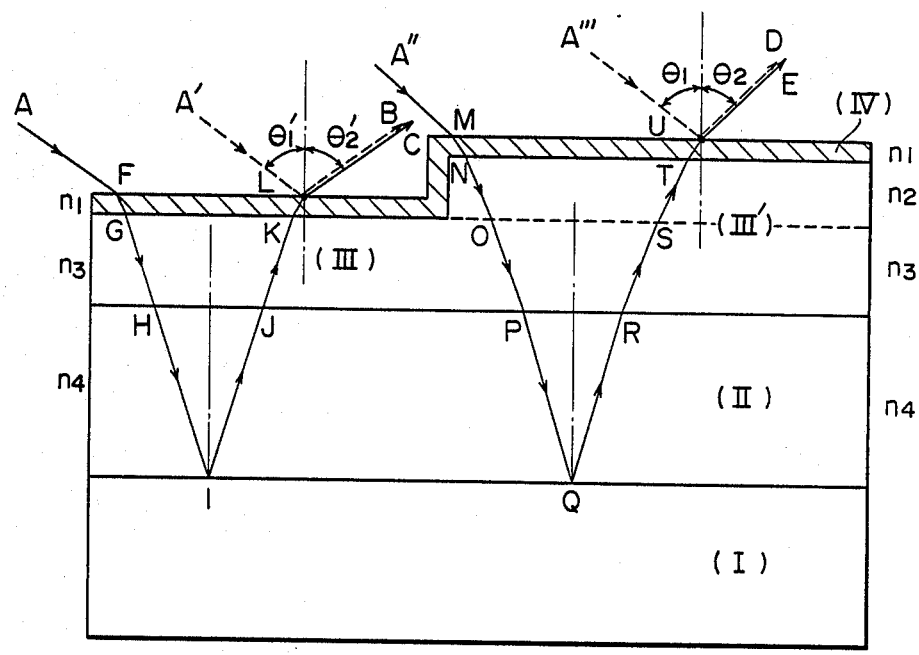
FIG. 1 is a view explaining light interference of a biological assay sample.
Figures 2A, 2B, 2C:
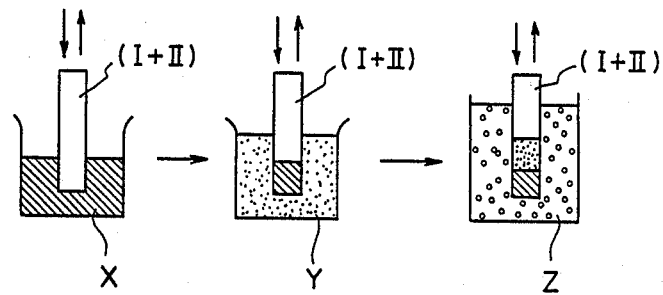
FIG. 2 is a side elevation showing an example of building a device with multiantibodies for detecting plural biological components, in the stages shown in FIGS. 2A, 2B and 2C.

In the accompanying drawings:

FIG. 1 is a view for explaining the concept of light interference of a biological assay sample, and FIG. 2 is a side elevation showing an example of building a device wih multiantibodies for detecting plural biological components. In the drawings, I represents a light reflecting substrate; II, a light interference layer; III, a layer of a substance for detecting a biological component; III', a complex layer formed by reaction of the layer III with the biological component to be detected; IV, a light transmitting reflecting layer; $n_1$, the refractive index of the light-transmitting reflecting layer; $n_2$, the refractive index of the biological component to be detected; $n_3$, the refractive index of the substance for detecting the biological component; $n_4$, the refractive index of the light interference layer; $\theta_1$ and $\theta_1'$, angles of incidence; and $\theta_2$ and $\theta_2'$, reflection angles.

The light reflecting substrate (I) used in this invention may be made of an ordinary metal such as iron, nickel, cobalt, zinc, titanium and bismuth, an alloy thereof, or a metal having a high reflectance such as gold, silver, copper and aluminum. The substrate (I) may be made of such a material itself in a plate form, or may be made by forming a thin layer of such metals or alloys, either singly or to improve adhesion to the substrate, in combination, by vapor deposition or sputtering on a solid substrate such as a glass plate or a plastic plate. The reflectance of this layer is at least 50%, preferably at least 70%, when white light is allowed to fall upon it at an incidence angle of 0 to 50 degrees, preferably 0 to 30 degrees.

The light interference layer (II) used in this invention should meet the following requirements (1) to (3). (1) It should not have substantial reflecting characteristics to visible light (wavelength 300 to 800 nm). (2) The thickness and refractive index of the light interference layer (II) should be controlled such that an increase in the thickness of the layer (III) of a substance for detecting a biological component with the biological component detecting reaction appears as a change in interference color. (3) Its surface preferably has sufficient affinity for the layer (III).

The light interference layer (II) may be made of an organic or inorganic material. The organic material may be any which does not substantially have reflecting or absorbing characteristics in a visible light region (300 to 800 nm) and are film-forming. Preferably, it may be an organic material which permits control of its film thickness to the order of 50 to 100 Å so as to induce efficient changes in the color of light interference with an increase in the thickness of a protein film by a biological component detecting reaction such as an antigen-antibody reaction to be described in detail hereinafter. Such organic materials may, for example, be compounds capable of forming a stable condensed monomolecular film on a water surface, such as long-chain carboxylic acids and metal salts and esters thereof, and materials capable of forming films having a thickness of not more than 2,000 Å by coating or vapor deposition. Specific examples of the former include long-chain saturated and unsaturated carboxylic acids such as palmitic acid, stearic acid, lignoceric acid, oleic acid and omega-tricosanoic acid, esters thereof, and salts thereof with mono- to tri-valent metals. Examples of the latter include vinyl polymers such as poly(methyl (meth)acrylate), polystyrene, poly(meth)acrylonitrile and polyvinyl chloride; polyolefins such as polyethylene, polypropylene and poly-4-methyl-pentene-1; and condensation polymers such as polyamides and polyesters. Since these substances induce effective light interference according to their refractive indices, their film thickness is controlled. The inorganic material which may constitute the light interference layer should likewise have no reflection and no absorption in the visible light region, and the thickness of a film thereof should be controlled to the order of 50 to 100 Å. Examples of the inorganic material having such properties include metal oxides such as silicon oxide, aluminum oxide, tin oxide, lead oxide, tungsten oxide, magnesium oxide, cobalt oxide, molybdenum oxide, titanium oxide, zirconium oxide, zinc oxide and tantalum oxide; metal fluorides such as calcium fluoride, magnesium fluoride and lithium fluoride; intermetallic compounds such as galliumarsenic; and silicon nitride. Such a material may be formed into a film of the desired thickness according to its refractive index by vapor deposition or sputtering and provided as the light interference layer (II) on the reflecting substrate (I).

Figure 3:
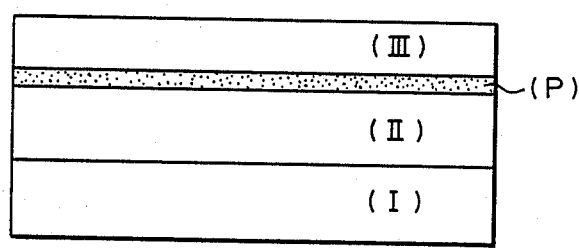
FIG. 3 is a sectional view showing how a substance for detecting a biological component can be fixed to a light interference layer.

The surface of the light interference layer (II) should also be required to have affinity for substances (such as antigens or antibodies) for detecting biological components in the layer (III). For this purpose, the surface of the light interference layer (II) may be treated by a hydrophobizing agent such as an alkyl- or aryl-silane, or chemically modified by a reactive compound which can chemically fix the substance for the detection of biological component to interference layer (II). The hydrophobizing agent layer and the reactive compound layer are shown as layer (P) in FIG. 3 (a sectional view similar to FIG. 2). The hydrophobizing agent layer is essential when the light interference layer is composed of an inorganic material.

Examples of the alkyl- or aryl-silane as the hydrophobizing agent are $C_{12}$–$C_{20}$ alkyltrichlorosilanes such as octadecyltrichlorosilane, mono-, di- or tri-alkoxysilanes, dimethyldichlorosilane, dimethylphenylchlorosilane and methyldiphenylchlorosilane.

The treatment of forming the reactive interlayer is carried out, as required, in order to increase the affinity of the surface of the light interference layer (II) for the biological component detecting substance in the layer (III).

In most known devices for detecting an immunological reaction utilizing light interference, antigen molecules are fixed, and there is no example in which an antibody is fixed in such devices. Since generally there are many recognition sites in antigen molecules, the alignment of the antigen molecules is not of much significance in fixing them. On the other hand, since the recognition sites of antibody molecules are strictly limited, they have to be arranged so that the recognition sites are effectively exposed to the surface of the detecting device. By an ordinary physical adsorption method or a chemical fixing method, it is extremely difficult to fix antibody molecules without impairing their activity.

In view of the above background, the present inventors have extensively worked on a method and a device for detecting an antigen-antibody reaction with good sensitivity by a simple procedure within a short period of time, and consequently found that an immunological detecting device of high sensitivity and free from delamination can be obtained by using a device consisting of a light reflecting substrate and a light interference layer having an optimized thickness and an optimized refractive index and chemically bonding an antibody layer to the surface of the light-interference layer selectively at sites other than the recognition sites of the antibody.

As one embodiment, the present invention provides a simple immunological detecting device comprising a light reflecting substrate (I) substantially free from diffused reflection, a light interference layer (II) laminated to the surface of the substrate (I), a reactive interlayer (P) formed on the layer (II) and composed of a compound capable of selectively reacting the carboxyl group or thiol group contained in antigen or antibody molecules or fragmented antibody molecules mainly by pH adjustment, and a layer (III) of an antigen substance and/or an antibody protein composed substantially of a monomolecular layer formed on the interlayer (P); and a method of immunological detection utilizing the device.

The compound capable of reacting with the carboxyl group of the protein is preferably one which contains functional groups such as

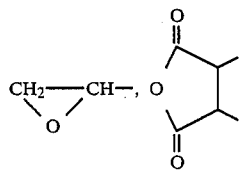

or $-NH_2$ in the molecule and can be fixed at a high density to the light interference layer. It may be a low-molecular-weight or high-molecular-weight compound. Specific examples of the low-molecular-weight compounds are

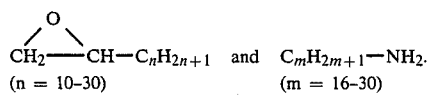

Specific examples of the high-molecular-weight compound are

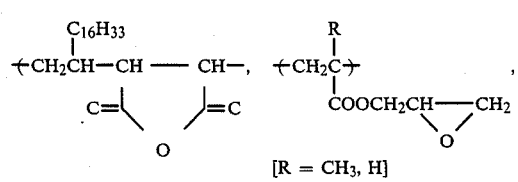

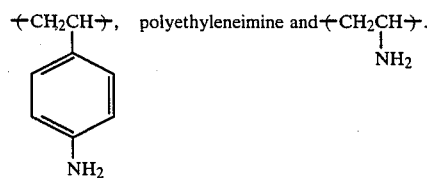

Compounds capable of reacting with the thiol group (SH) of the protein are, for example,

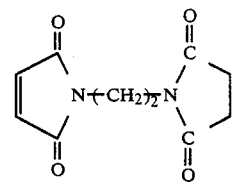

(when this compound is used, the substrate is preferably pre-treated with, for example,

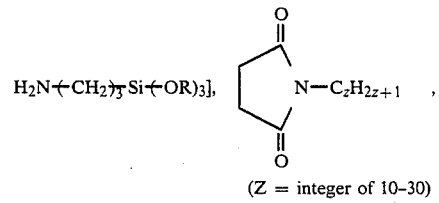

(Z = integer of 10-30)

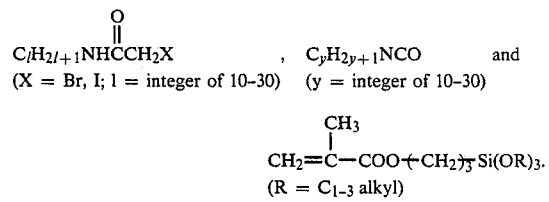

(X = Br, I; l = integer of 10-30)  (y = integer of 10-30)

$$CH_2=\overset{CH_3}{\underset{|}{C}}-COO(CH_2)_{\overline{x}}Si(OR)_3.$$

(R = $C_{1-3}$ alkyl)

N-substituted maleimide is most preferably used. Many of the above compounds can react not only with the carboxyl or thiol groups in the protein but also with the amino groups in it. Hence, the protein fixing reaction should be carried out by adjusting the pH of the reaction system. The preferred pH range is 3 to 5 for the reaction with the carboxyl groups, and 4 to 6 for the reaction with the thiol groups.

Such a compound is formed as a thin film layer (P) on the light interference layer (II). The thickness of this film should be controlled such that the interference color of the entire layer above the light reflecting substrate should be within the visible light region. Such a film thickness is selected from 25 to 5000 Å, preferably 30 to 3,000 Å.

The thickness of the light interference layer (II) should be selected such that when the incidence angles $\theta_1$ and $\theta'_1$ are 0 to 50 degrees, the light path differences of the incident light at the device as shown in FIG. 1, Light path difference $-1$:

$$n_1 \times (\overline{FG} + \overline{KL}) + n_3 \times (\overline{GH} + \overline{KJ}) + n_4 \times (\overline{HI} + \overline{IJ})$$

Light path difference $-2$:

$$n_1 \times (\overline{MN} + \overline{UT}) + n_2 \times (\overline{NO} + \overline{ST}) +$$
$$n_3 \times (\overline{OP} + \overline{RS}) + n_4 \times (\overline{PQ} + \overline{QR})$$

become the product of the wavelengths of incident lights multiplied by integers. Furthermore, for the discrimination of an antigen-antibody reaction site, it is convenient that the light path difference $-1$ differs from the light path difference $-2$. For example, the optical thickness of the light interference layer (II) should be controlled to about 500 to 5,000 Å, preferably 700 to 3,000 Å, when this layer has a refractive index of 1.4 to 2.0. Examples of such an accurate film thickness controlling method are the Langmuir-Blodgett method (a monomolecular film on a water surface is accumulated on a solid substrate), the spin coat method, the vapor deposition method and the sputtering method.

The biological component detecting substance in the layer (III) to be fixed to the light interference layer (II) may preferably be antibodies, antigens, etc. which are involved in immunological reactions, nucleic acids, viruses, bacteria, etc. Of these, the antigens and antibodies are preferred.

Examples of the antigens are immunoglobulins such as IgG, IgA, IgE and IgM, human chorionic gonadotropin (HCG), and carcinoembryonic antigen (CEA). As the antibodies, polyclonal or monoclonal antibodies to these antigens are used.

These antigens or antibodies may be fixed to the surface of the light interference layer (II) [the term "light interference layer (II)", to be used hereinbelow, means one optionally having the aforesaid hydrophobizing agent layer or reactive interlayer (P) on its surface]by immersing the device in an aqueous solution of an antigen or antibody for 0.5 to 20 hours, and then fully washing it with water to remove the antigen (or antibody) molecules physically adhered to it. As a result of this adsorption treatment, the antigen (or antibody) is fixed onto the light interference layer (II) as a monomolecular layer (III).

One or more kinds of antibodies and/or antigens may be adsorbed on the light interference layer (II). To fix two or more kinds of antibodies (or antigens), the depth of chips (I+II) composed of the reflecting substrate (I) and the light interference layer (II) formed thereon, to which they are immersed in solutions (X, Y and Z) of the antibodies (or antigens), is progressively increased. By so doing, it is possible to fix a plurality of antibodies (or antigens) onto the same chip as a monomolecular layer since generally, another antibody (or antigen) is not adsorbed on that part to which one antibody (or antigen) has adhered. This procedure enables expensive monoclonal antibodies, for example, to be effectively fixed.

According to another preferred embodiment of this invention, the antibody protein layer (III) can be fixed to the light interference layer (II) in a form oriented so that it does not lose activity, by spreading (1) a monomolecular film of a long-chain fatty acid having 24 to 32 carbon atoms, a salt thereof with a polyvalent metal and/or an ester thereof or (2) a monomolecular film of a polyvalent metal salt of a long-chain fatty acid having 14 to 23 carbon atoms and/or an ester of the long-chain fatty acid on an aqueous phase surface, and contacting a water-soluble antibody protein dissolved in the aqueous phase to form an antibody monomolecular mixed film on the interface of the aqueous phase, and laminating the complex on the light interference layer (II).

The antibody protein generically denotes a water-soluble protein which can induce an antigen-antibody reaction, and contains an antigen recognition site (Fab for short) and a hydrophobic terminal site (Fc for short).

Specific examples of the antibody protein are immunoglobulins G (abbreviated IgG), IgE, IgM and antibodies to them, human chorionic gonadotropin (HCG) antibody and carcinoembryonic antigen (CEA) antibody.

In fixing these antibody proteins, care should be taken not to denature the Fab portion. In conventional fixing procedures by a chemical reaction, the Fab portion is also involved in the reaction to cause a decrease in the activity of the antibody protein. According to the above method in accordance with this invention, the antibody protein is incorporated at a high density into the monomolecular film while hydrophobically interacting at the Fc site or adsorbed on and fixed to the monomolecular film while maintaining high immunological activity.

The monomolecular film preferably remains a condensed monomolecular film on a solid on a water surface and does not substantially dissolve in water. Examples of the long-chain fatty acid having 24 to 32 carbon atoms, its polyvalent metal salt and/or its ester include lignoceric acid ($C_{23}H_{47}COOH$), cerotic acid ($C_{25}H_{51}COOH$), montan acid ($C_{27}H_{55}COOH$) melissic acid ($C_{29}H_{59}COOH$), lacceronic acid ($C_{13}H_{63}COOH$), polyvalent metal salts of long-chain fatty acids represented by the formula $C_nH_{2n+1}COOM$ ($n=23-31$, $M=$ a polyvalent metal ion such as alkaline earth metals, cadmium and aluminum), and esters of these fatty acids with methanol or ethanol. Examples of the polyvalent metal salts of long-chain fatty acids having 14 to 22 carbon atoms and/or the esters of these fatty acids are salts of polyvalent metals such as alkaline earth metals, cadmium, and aluminum with fatty acids such as myristic acid ($C_{13}H_{27}COOH$), palmitic acid ($C_{15}H_{31}COOH$), stearic acid ($C_{17}H_{35}COOH$) arachidic acid ($C_{19}H_{39}COOH$) and behenic acid ($C_{21}H_{43}COOH$), and esters of these fatty acids with methanol or ethanol.

The above compound (1) or (2), either as a carboxylic acid or its ester, is dissolved in an organic solvent such as benzene or chloroform to form a solution having a concentration of 0.5 to 1.5 millimoles/liter. When the solution is spread on the surface of distilled water or an aqueous solution containing a polyvalent metal salt (such as barium chloride, cadmium chloride or aluminum chloride), the monomolecular film used in this invention is formed. The monomolecular film is then compressed so that its surface pressure becomes 1 to 20 mN/m, and under these compressing conditions, the antibody protein is injected into the aqueous phase below the film. By keeping the antibody protein and the monomolecular film on the water surface in contact with each other for a predetermined period of time (usually 30 minutes to 1 hour), complexing of the protein and the monomolecular film is completed. At this time, the complex film of the antibody protein and the monomolecular film is again compressed to a surface pressure of 10 to 30 mN/m, and laminated to the surface of the light interference layer (II) by the Langmuir-Blodgett or the horizontal lifting method. One or more layers of such complex film can be laminated.

The amount of the antibody protein fixed to the light interference layer is calculated from the ratio of the water surface area of the spread film to the area of the light interference layer at the time of lamination and the intensity of the UV absorption spectrum of the film.

At least a region of the detection device of this invention in which the layer (III) is fixed is brought into contact with an assay sample to be determined to contain a biological substance such as an antigen (or antibody) to thereby allow a biological reaction to take place. Consequently, a layer (III') of a complex of the biological component to be detected and the biological component detecting substance is formed on at least a region (the region where the reaction has taken place) on the layer (III) (the device in this condition is referred to as a "detection structure").

Preferably, the biological component to be detected is selected so that as a result of complexing, an increase in its optical thickness becomes more than 5 Å, preferably more than 10 Å, but less than 500 preferably less than 300 Å. Antigens and antibodies are preferred as such a component.

The present invention is applicable even when the biological component to be detected is the same as the substance of the biological component detecting substance layer (III). For example, if it is an antigen, an antibody to the biological component (antigen) is used as an intermediary substance. By mixing this antibody with a solution suspected of containing the biological component to be detected, and contacting the mixture with the device, the antibody reacts competitively with the biological component in the solution and the biological component in the device. The advantage of this method is that the above antibody subjected to a contrast enhancement treatment in advance can be used, and this can increase detection sensitivity. Furthermore, the activity of the device is easy to retain because it is an antigen which is to be fixed to the device and not an antibody that is more susceptible to deactivation than antigen in fixation.

In the detecting method of this invention, a light-transmitting reflecting layer (IV) is then formed on the surfaces of the layers (III') and (III). Formation of the layer (IV) permits very easy distinction between the portion where the biological reaction has taken place (III')) and the other portion where no biological reaction has taken place [(III)] on the detection structure.

Preferably, the light-transmitting reflecting layer (IV) is a thin layer of a metal, preferably a noble metal, formed by a vapor deposition method, other physical vapor deposition methods, a colloidal particle coating method, etc. The colloidal particle coating method is preferred because of its simplicity of operation. Metal colloids which exist stably in water, can be adsorbed on, or react with, proteins, and have a particle diameter of 10 to 200 Å, preferably 30 to 150 Å, can be used in this method. Specific examples include dispersions of fine particles of gold, platinum, silver, palladium, ruthenium, aluminum, copper, nickel, iron, etc., either alone or together with dispersion stabilizers, in water. Gold colloid is most suitably used in this invention. These metal colloids form a high reflectance layer on the surface of the detection structure and strikingly improves the visual determinability of the device.

To increase visual determinability further by gold colloid, the conditions for coating gold colloids may be controlled by considering the isoelectric points of proteins adhering to the device. The gold colloid has the property of being adsorbed on a protein at a pH slightly (less than 1.0, preferably about 0.5) higher than the isoelectric point of the protein. If the gold colloid is adsorbed at a pH about 0.5 higher than the isoelectric point of a protein to be detected and lower than, or more than 1.0 higher than, the isoelectric point of a detecting protein, only the protein is colored by the metal colloid adsorbed thereon, and the other portion is not colored (or hardly colored), and the presence of the protein can be determined very easily.

Generally, since the concentration of the protein to be detected is low, it is preferred from the standpoint of detection sensitivity to operate so that the gold colloid is adsorbed on the protein to be detected.

The light-transmitting reflecting layer (IV) formed in the above manner has a thickness of 30 to 300 Å, preferably 50 to 100 Å, and its light reflectance is 10 to 40%, preferably 20 to 30%, at an incidence angle of 0 to 50 degrees.

Figure 4:
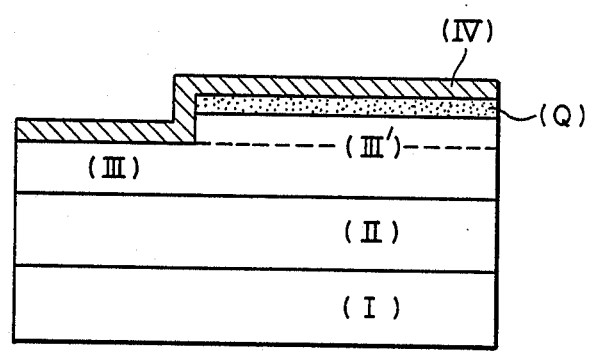
FIG. 4 is a sectional view showing an embodiment for increasing the detection sensitivity of a device.

As one modification, it is possible to first subject the surface of the layer (III') of the detection structure to a contrast enhancement treatment, and then provide the light-transmitting reflecting layer (IV). In this treatment, a substance capable of reacting with the substance to be detected, with which the substance in the biological component detecting substance layer (III) reacts, at a site different from the site at which the substance to be detected reacts may be used as a contrast enhancement agent. The molecular size of the contrast enhancement agent is selected so that after reaction with the substance to be reacted, the light interference color of the device varies in a visible light region. As a specific example, its thickness is 30 to 200 Å, preferably 50 to 150 Å. Its molecular sectional area is not particularly restricted, but is generally 0.05 to 3 micrometers, preferably 0.1 to 1 micrometer. Specific examples include secondary antibodies, enzyme-labelled secondary antibodies, secondary antibodies fixed to emulsions and secondary antibodies fixed to latices. When the contrast enhancement agent is added after the biological component detecting substance layer (III) has reacted, or is reacting, with the substance to be detected on the device, a layer (Q) of the contrast enhancement agent is formed on the layer (III') as shown in FIG. 4 (sectional view), and these layers as a whole increase in optical thickness to increase the detection sensitivity of the device.

When, for example, white light is allowed to fall upon the detection structure formed as above by using the device of this invention at an incidence angle of, for example, 0 to 50 degrees, the site where the antigen-antibody reaction has taken place can be clearly detected by the change in the interference color of the reflected light. Furthemore, when monochromatic light is allowed to fall, the site of the antigen-antibody reaction can be detected by distinguishing the brightness and darkness of the reflected light. The sensitivity of its detection is much higher than that obtained with conventional devices and methods. An antibody (or antigen) in a concentration of $10^{-5}$ to $10^{-12}$ to mole/liter can be clearly detected by visual inspection within several minutes to 30 minutes.

The requisites used in the detecting method of this invention are all handy and simple. These requisites can therefore be offered to the consumers in the form of a kit composed of, for example, (1) a pack of various types of the device described above and (2) a pack of metal colloid, and optionally (3) a pack of a contrast enhancement agent.

If it is desired to perform quantitative determination at higher detection sensitivity in the above detection, it is possible to detect changes in light interference as the amount of change in color difference. Generally, the color difference is typically represented by the following equation ($\Delta E^*ab$) defined by tristimulus values X, Y and Z of the visible spectrum of the calorimetric standard observer stipulated by International Committee on Illumination (ICI).

$$\Delta E^*ab = \sqrt{(\Delta L^*)^2 + (\Delta a^*) + (\Delta b^*)^2}$$

$$\text{wherein } L^* = 116 \left(\frac{Y}{Y_o}\right)^{\frac{1}{3}} - 16,$$

-continued $$a^* = 500\left[\left(\frac{X}{X_o}\right)^{\frac{1}{3}} - \left(\frac{Y}{Y_o}\right)^{\frac{1}{3}}\right],$$

$$b^* = 200\left[\left(\frac{Y}{Y_o}\right)^{\frac{1}{3}} - \left(\frac{Z}{Z_o}\right)^{\frac{1}{3}}\right],$$

$X_o$, $Y_o$ and $Z_o$ are tristimulus values of an illuminating light source, and X, Y and Z are tristimulus values of the spectrum of the calorimetric standard observer stipulated by International Committee on Illumination (1931).

Among the color components constituting the color differences $\Delta E^*ab$, $\Delta L^*$, $\Delta a^*$ and $\Delta b^*$ respectively represent the amount of change of the brightness ($L^*$) of color, the amount of change of a red color component ($a^*$) and the amount of change of a yellow color component ($b^*$). According to the standards of ICI, an absolute value of the color difference ($\Delta E^*ab$) of 0 to 0.5 means that determination of the color difference by visual inspection is impossible or the color difference is very slight; an absolute value of the color difference of 1.0 to 6.0 means that the color difference by visual observation can be determined; an absolute value of the color difference of 6.0 to 12.0 means that the color difference is very remarkable; and an absolute value of the color difference of more than 12.0 means that the color is of another color series. Hence, when in the detecting method of this invention, the color difference, $\Delta E^*ab$, between the reacted site (III′) and the unreacted site (III) is 0.1 to 1.0, more strictly 0.1 to 0.5, distinction by visual inspection is difficult. In this case, it is desirable to perform quantitatvve distinction by a color difference photometer. Systems utilizing other conversion equations for color difference may of course be used.

To increase the luminance of the light interference color, it is preferred to use an incidence light source having the strongest possible intensity. If, however, the intensity of the incident light is too strong, direct visual inspection becomes impossible. When a color difference photometer is used, such physiological restrictions on the light intensity are obviated and therefore desirable light intensities can be used.

Detection can be performed with the highest sensitivity by designing the device such that the angle of incident light on the detection structure or the angle between the detection structure and a light-receiving section in a color difference photometer is optimal, or it can be adjusted so as to provide such an optimal angle difference.

Since the color difference by the interference light can be displayed digitally by the color difference photometer, discrimination does not differ among the testing persons, and the detection device can be handled with rapidity, simplicity and convenience. Preferably, the color difference photometer includes a light source or a jig for diffusing and reflecting or radiating the incident light, such as a bulb for multiple light reflection and a light diffusion plate, a photovoltaic element, and a color difference data processor. Specifically, there may be used a method which comprises separating an interference spectrum measured on the surface of the detection structure into tristimulus value components of light and analyzing them, and a method in which the tristimulus values of interference light are calculated by also including a sensor which measures the reflected light from the detection structure having sensitivity corresponding to the spectral sensitivity of the human eye and also detects the spectral sensitivity of the illuminating light source. The color difference limit of these color difference meters is $\pm 0.15$ in terms of $\Delta E^*ab$.

The present invention enables a biological component to be detected (an antigen, an antibody, etc.) in a low concentration within short periods of time with good sensitivity, simplicity and convenience, and is of great significance in practical applications.

The following non-limitative examples illustrate the present invention more specifically.

EXAMPLE 1

An $SiO_2$ target and a chrome-plated stainless steel plate as a substrate were set in a chamber in a high-frequency sputtering device, and the inside of the chamber was evacuated to a pressure of $1 \times 10^{-5}$ torr. Ar (100%) gas was introduced into the chamber. The pressure of the inside of the chamber was maintained at $1.0 \times 10^{-3}$ torr, and glow discharge was performed at 500 W for 13 minutes to form an $SiO_2$ layer having a thickness of 800 Å on the surface of the chrome-plated substrate. The chromeplated stainlesss steel plate having the $SiO_2$ layer with a thickness of 800 Å was immersed for 2 hours in a $1.0 \times 10^{-2}$ wt. % chloroform solution of octadecyltrichlorosilane to hydrophobize the surface of the $SiO_2$ layer. The plate was then immersed for 12 hours in an aqueous human IgG solution ($5 \times 10^{-2}$ mg/ml). The resulting device was immersed for 5 minutes in an aqueous solution of sheep anti-human IgG (specific to H and L chains) in a concentration of $5 \times 10^{-2}$ mg/ml to prepare a detection structure.

When the detection structure was visually inspected from an angle of 70 degrees, the surface of the $SiO_2$ layer showed an interference color of pale yellow, the human IgG-adsorbed surface showed an interference color of yellow, and the anti-human IgG reacted surface showed an interference color of red. However, when it was visually inspected from an angle of 30 degrees, it was very difficult to determine these interference colors.

The detection structure was then immersed for 20 minutes in an aqueous solution of gold colloid having a particle diameter of 5 nm ($6.5 \times 10^{14}$ particles/ml) for 20 minutes, washed with distilled water, and dried. When the resulting structure was visually inspected from an angle of 30 degrees, the surface of the $SiO_2$ layer showed an interference color of yellow, the human IgG-adsorbed surface showed an interference color of orange, and the anti-human IgG reacted-surface showed an interference color of violet. The ease of visual inspection was thus increased greatly.

EXAMPLE 2

In the same way as in Example 1, an $SiO_2$ layer having a thickness of 800 Å was formed on a chrome-plated stainless steel plate by the high-frequency sputtering method. As in Example 1, a human IgG-adsorbed surface and an anti-human IgG-reacted surface were prepared on the resulting plate. No interference color was observed in any of these surfaces at a glancing angle of 0 to 30 degrees.

Then, a thin film of gold having a thickness of 50 to 75 Å was formed on the resulting plate by vapor deposition, clear interference colors could be viewed.

When the thin gold film was prepared by high-frequency sputtering, clear interference colors could likewise be observed.

COMPARATIVE EXAMPLE 1

Example 1 was repeated except that a silicon wafer (reflectivity for perpendicular incident light: 40%) was used instead of the chrome-plated stainless steel plate (ibid.: 90%) as a substrate. By immersing the resulting device in a gold colloid solution, the ease of visual inspection of changes in interference colors increased. But the colors had a darker tone than in the case of using the chrome-plated stainless steel substrate, and visual inspection was more difficult.

EXAMPLE 3

Example 1 was repeated except that a polyethylene terephthalate film (thickness 50 microns) having aluminum vapor-deposited thereon to a thickness of 1,000 Å was used instead of the chrome-plated stainless steel substrate. By immersing the resulting device in a gold colloid solution, the ease of visual inspection of changes in interference colors was greatly increased.

EXAMPLES 4–7

In Example 1, an aqueous solution (pH 9: adjusted with NaOH aq.soln.) of each of the metal colloids shown in Table 2 was used instead of the aqueous gold colloid solution. Specifically, the detection structure obtained after the antigen-antibody reaction was immersed in the metal colloid solution for 30 minutes, and the interference color of the antibody-fixed site and the interference color of the antigen-antibody reaction site were compared. In all runs, a clear color difference could be visually determined. The difference ($\Delta Eab$) between the color of the antibody-fixed site and the color of the antigen-antibody reaction site was measured by a color difference photometer including a bulb for multiple light reflection, a photovoltaic element and a color difference data processor self-recording spectral photometer of Hitachi Limited (with an accessory device having a U-3200/3400 type); measuring wavelength, 380–780 nm; incidence angle, 6 degrees; visual field angle 10 degrees; calculated for standard A light). Clear color differences were observed as shown in Table 1.

TABLE 1

| Example | Metal colloid (*1) | Changes in interference colors after the antigen-antibody reaction (*2) | |
|---|---|---|---|
| | | Visual determinability | Color difference ($\Delta Eab$) |
| 4 | platinum | very clear | 1.68 |
| 5 | silver | very clear | 1.45 |
| 6 | palladium | very clear | 1.24 |
| 7 | ruthenium | very clear | 1.10 |

(*1): Metal colloids for atomic absorptiometry (special reagent grade made by Wako Pure Chemicals, Co., Ltd.).
(*2): Using the anti-human IgG-fixed device, $10^{-8}$ M of human IgG was detected.

EXAMPLES 8–11

As a light interference layer, a thin film of each of the inorganic compounds indicated in Table 2 was vapor-deposited on a chrome-plated stainless steel substrate. The light interference layer was treated with octadecyltrichlorosilane in the same way as in Example 1 and then anti-human IgG antibody was adsorbed and fixed on and to the treated light interference layer. Using the resulting device, human IgG was detected in the same way as in Example 1. The interference colors observed at a glancing angle ($\theta_2$) of 60 to 70 degrees are shown in Table 2. When a thin film of gold colloid was coated on the surface of the detection structure in the same way as in Example 1, at a glancing angle of 0 to 30 degrees, the surface looked deep violet, and its visual determinability increased greatly.

TABLE 2

| | Inorganic compound | | Change in color before and after the antigen-antibody reaction (before treatment with god colloid) | After treatment with gold colloid |
|---|---|---|---|---|
| Example | Type | Film thickness (Å) (*) | | |
| 8 | silicon dioxide | 590 | yellow orange to red | deep violet |
| 9 | aluminum oxide | 650 | scarlet to violet | deep violet |
| 10 | tin oxide | 820 | red to blue | deep violet |
| 11 | magnesium fluoride | 1059 | yellow to scarlet | deep violet |

(*) Measured by an ellipsometer (DVA-361, Mizoshiri Kogaku).

EXAMPLE 12

A stainless steel plate having a vapor deposited silver layer (thickness 500 Å) and an $SiO_2$ layer having a thickness of about 1000 Å was immersed for 2 hours in a $1.0 \times 10^{-2}$ wt. % chloroform solution of octadeccyltrichlorosilane to hydrophobize the surface of the $SiO_2$ layer. Part of the plate was immersed for 12 hours in a human IgG solution ($5 \times 10^{-2}$ mg/ml). Part of the resulting device was immersed for 5 minutes in a solution of sheep antihuman IgG (specific to H and L chains) in a concentration of $5 \times 10^{-2}$ mg/ml) to prepare a detection structure. A gold colloid film was applied to the detection structure in the same way as in Example 1. The diffusion reflection spectrum of the structure was measured by using the same color difference photometer as used in Examples 4 to 7, and the color difference between the human IgG-adsorbed surface and the anti-human IgG reacted surface was measured. $\Delta E^*ab$ was 2.71, and $\Delta L^*$, $\Delta a^*$ and $\Delta b^*$ were 2.39, $-0.88$, and 0.93, respectively. The color difference between the human IgG-adsorbed surface and the anti-human IgG-reacted surface could be determined by the difference in the brightness of color ($\Delta L^*$).

EXAMPLE 13

Part of the human IgG-adsorbed portion of the device prepared in Example 12 was immersed in an aqueous solution of anti-human IgG ($3 \times 10^{-10}$ mole/liter), and then a thin gold colloid film having a thickness of 50 to 70 Å was formed on the surface of the device. Changes in interference color on the surface of the device could be visually determined only with difficulty. When it was immersed in an aqueous solution of anti-human IgG ($3 \times 10^{-11}$ mole/liter), the changes in interference color could not be determined visually.

The color difference between the human IgG-adsorbed surface and the anti-human IgG-reacted surface of this detection structure was measured by a color difference photometer in the same way as in Example 12. $\Delta E^*ab$ was 2.14, and $\Delta L^*$, $\Delta a^*$ and $\Delta b^*$ were 1.88, $-0.54$, and 0.85, respectively. The color difference between the human IgG-adsorbed surface and the antihuman IgG-reacted surface could be determined by the difference in the brightness of color ($\Delta L^*$).

EXAMPLE 14

In measuring the color difference between the human IgG adsorbed surface and the anti-human IgG-reacted surface in Example 12, there was used another color difference photometer (CR-200, Minolta Color Difference Photometer) including a sensor having sensitivity corresponding to the spectral sensitivity of the human eye and a sensor for detecting the spectral sensitivity of an illuminating light source, and the color difference was determined by calculating the tristimulus values of interference colors. $\Delta E^*ab$ was 2.75, and $\Delta L^*$, $\Delta a^*$ and $\Delta b^*$ were 2.40, $-1.04$, and 0.89, respectively. The color difference between the human IgG-adsorbed surface and the anti-human IgG-reacted surface could be determined by the difference in the brightness of color ($\Delta L^*$).

EXAMPLE 15

A chrome-plated stainless steel plate having an $SiO_2$ layer with a thickness of 1000 Å was immersed for 2 hours in a a $1.0 \times 10^{-2}$ wt. % chloroform solution of octadecyltrichlorosilane to hydrophobize the surface of the $SiO_2$ layer.

This substrate was immersed for 12 hours in a solution of polyclonal anti-human IgG ($5 \times 10^{-5}$ g/ml). It was further immersed for 5 minutes in a solution of human IgG (specific to H and L chains) in a concentration of $5 \times 10^{-9}$ g/ml (which is two orders of magnitude lower than the concentration of the assay solution used in Example 1).

The device was further kept in contact with an aqueous solution of polyclonal anti-human IgG ($5 \times 10^{-5}$ g/ml) for 30 minutes.

When the so treated substrate was visually observed from an angle of 70 degrees, the surface of the $SiO_2$ layer showed an interference color of pale yellow, the anti-human IgG-adsorbed surface showed an interference color of yellow, and the human IgG-reacted surface showed an interference color of red violet.

The substrate was then immersed for 20 minutes in a solution of gold colloid having a particle diameter of 5 nm ($6.5 \times 10^{14}$ particles/ml). By visual inspection from an angle of 30 degrees, the surface of the $SiO_2$ layer showed an interference color of yellow, the anti-human IgG-adsorbed surface showed an interference color of orange, and the anti-human IgG-reacted surface showed an interference color of blue violet. The ease of visual inspection increased.

EXAMPLE 16

Stearic acid (8 mg) was dissolved in 1 ml of distilled chloroform. The solution (200 microliters) was gradually added dropwise by means of an ultramicropipette onto an aqueous solution of barium chloride ($3 \times 10^{-5}$M) and potassium hydrogen carbonate ($4 \times 10^{-4}$M) filled in a vessel (surface area 491.4 cm$^2$) for measuring a surface pressure-area curve (to be referred to as a $\pi$-A curve). After the addition, it was left to stand for 5 minutes, and a partition plate in the vessel was moved until the surface pressure became 20 mN/m.

The film spread on the water surface was maintained at a surface pressure of 20 mN/m, and accumulated in 35 layers (film thickness of 850 Å) on a chrome-plated stainless steel plate (mirror-surface finished) subjected to a hydrophobizing treatment (coating of iron (III) stearate) by a vertical immersion method (to be referred to as the LB method). At this time, the substrate showed an interference color of yellow owing to the presence of barium stearate accumulated films. One layer of a monomolecular film of N-octadecyl maleimide spread on a water surface in advance was accumulated on the barium stearate layers by a horizontal lifting method. The substrate showed an interference color of yellow orange.

The substrate was then immersed in a solution of sheep anti-human IgG (specific for H and L chains) in a concentration of 0.4 mg/ml for 2 hours. The interference color of the surface of the device became red, showing that the anti-human IgG was adsorbed on the substrate as a monomolecular layer. Furthermoe, the substrate was immersed in a human IgG solution ($5 \times 10^{-10}$ g/ml) for 2 hours. The color on the surface of the device after the antigen-antibody reaction of the anti-human IgG and the human IgG was difficult to distinguish. When the device was immersed in an aqueous emulsion of oleic acid having anti-human IgG adsorbed thereto in advance, the interference color at a visual angle of 60 to 70 degrees changed to blue violet and the antigen could be distinguished. When the surface of the device was treated with gold colloid as in Example 1, clearer distinction could be made at a glancing angle of 0 to 30 degrees.

EXAMPLE 17

In Example 16, the device after the antigen-antibody reaction was immersed in a polyethylene latex having anti-human IgG adsorbed and fixed on or to it instead of the oleic acid emulsion. The interference color of the reacted site changed to blue violet, and the antigen could be distinguished at a glancing angle of 60 to 70 degrees. When the surface of this device was treated with gold colloid, clearer distinction could be made at a glancing angle of 0 to 30 degrees.

EXAMPLE 18

A device was prepared in the same way as in Example 1 except that monoclonal anti-hCG ($5 \times 10^{-2}$ mg/ml) was fixed instead of human IgG. This device was immersed in an aqueous solution containing 10 ng/ml of hCG, and the antigen-antibody reaction was performed. When the device was treated with a gold colloid solution at a pH of 9. The antigen-antibody reaction site and the antibody-fixed site could be clearly distinguished by visual inspection with a color difference of pale blue violet and blue violet.

EXAMPLES 19-21

Example 18 was repeated except that each of the antigen-antibody combinations shown in Table 3 was used instead of the combination of monoclonal anti-hCG and hCG. The results are shown in Table 3.

TABLE 3

| Example | Detecting substance (antibody) | Substance to be detected (antigen: $10^7$ mole/liter) | Interference color Before gold treatment | After gold treatment |
|---|---|---|---|---|
| 19 | anti-$\alpha_2$-I | $\alpha_2$-PI | yellow orange | blue violet |
| 20 | anti-GST | GST | orange | blue violet |
| 21 | anti-protein C | Protein C | orange | blue violet |

EXAMPLE 22

Stearic acid (8 mg) was dissolved in 1 ml of distilled chloroform. The solution (200 microliters) was gradually spread dropwise by means of an ultramicropipette onto an aqueous solution of barium chloride ($3 \times 10^{-5}$M) and potassium hydrogen carbonate ($4 \times 10^{-4}$M) filled in a trough (surface area 491.4 cm$^2$) for measuring a surface pressure-area curve (to be referred to as a $\pi$-A curve). After the addition, it was left to stand for 5 minutes, and a moving barrier plate in the trough was moved until the surface pressure of the monomolecular film became 20 mN/m.

The film spread on the water surface was maintained at a surface pressure of 20 mN/m, and accumulated in 35 layers (film thickness of 850 Å) on a chrome-plated stainless steel plate (mirror-surface finished) subjected to a hydrophobizing treatment [coating of iron (III) stearate] by the LB method. At this time, the substrate showed an interference color of yellow owing to the presence of barium stearate accumulated films. One layer of a monomolecular film of N-octadecyl maleimide spread on a water surface in advance was accumulated on the barium stearate layers by the horizontal adhering method. The substrate showed an interference color of yellow orange.

The substrate was then immersed in a solution of sheep anti-human IgG (specific for H and L chains), into which 1 to 10 equivalents of SH groups had been introduced per antibody molecule, in a concentration of 0.4 mg/ml for 2 hours. The interference color of the surface of the device became red, showing that the anti-human IgG was adsorbed on the substrate as a monomolecular layer. Furthermore, the substrate was immersed in a human IgG solution (0.3 mg/ml) for 2 hours. The color on the surface of the device became violet as a result of adsorption of human IgG on the substrate by the antibody reaction of anti-human IgG and human IgG.

Thus, by using the aforesaid device, the presence of human IgG could be detected by visual inspection (at a visual field angle of 60 to 70 degrees) by changes in color. When the device was further treated with gold colloid, the presence of human IgG could be more clearly determined visually at a visual field angle of 0 to 30 degrees.

EXAMPLE 23

When 41 film layers (film thickness 1000 Å) of stearic acid were accumulated by the LB method on a chrome-plated stainless steel plate as in Example 22, the interference color of the substrate became red. A monomolecular film of

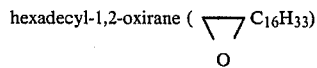

hexadecyl-1,2-oxirane previously compressed to 20 mN/m on a water surface was accumulated in one layer on the substrate. When this accumulated film was immersed for 4 hours in an anti-human IgG solution dissolved in aqueous NaCl adjusted in advance to pH 5.5, the color became violet. Furthermore, when it was reacted with human IgG, the color became blue. The interference color appeared with good reproducibility, and showed that the antibody protein was firmly fixed to the substrate by a chemical reaction. By treating the device further with gold colloid, the presence of the antibody protein could be more clearly inspected visually at a visual field angle of 0 to 30 degrees.

EXAMPLE 24

In Example 22, a device was prepared in the same way by using a 1:1 alternate copolymer of octadecene and maleic anhydride instead of octadecyl maleimide and spreading a chloroform solution (10 mg/25 mg) of this copolymer on a water surface. The carboxyl groups of anti-human IgG antibody were reacted and fixed at a pH of 5.5 on the resulting device, and then the device was immersed for 30 minutes in a dilute aqueous solution ($10^{-10}$ M/liter) of human IgG. The color of the surface of the device based on the light interference changed from red orange to violet (glancing angle 70 degrees). By treating the surface of the device with a gold colloid solution, the change in interference color could be visually determined more clearly at a glancing angle of 0 to 30 degrees.

EXAMPLE 25

A stainless steel plate (mirror-surface finished) having a silicon dioxide layer with a thickness of 1000 Å, which had been subjected to refluxing treatment in a 10% toluene solution of gamma-aminopropyltriethoxysilane for 8 hours, was immersed in a solution of N-(epsilon-maleimidecaproyloxy)succinimide in sodium phosphate buffer (0.1M, pH 7) in a concentration of $1 \times 10^{-3}$ mole/liter, and maintained at 30° C. for 45 minutes. Then, the stainless steel plate was washed with water. This stainless steel plate having a meleimide group was used as a substrate of a detection device.

Fifty microliters of 0.1M mercaptoethylamine solution (0.1M sodium phosphate, pH 6, containing 5 mM ethylenediaminetetraacetic acid) was added to 450 microliters of a 0.72% solution of F(ab')$_2$ of sheep anti-human IgG in sodium phosphate buffer (0.1M) pH 6), and the mixture was maintained at 37° C. for 90 minutes. The solution was purified by gel column chromatography to give a solution of Fab of sheep anti-human IgG (0.48 mg/ml).

The substrate of the device was immersed for 12 hours at 4° C. in a solution of Fab of sheep anti-human IgG ($4.8 \times 10^{-2}$ mg/ml). By this immersion, the interference color of the substrate changed from orange to red. This showed that the Fab of sheep anti-human IgG was fixed to the substrate. Then, the resulting substrate was immersed in a human IgG solution ($5 \times 10^{-3}$ mg/ml) for 30 minutes. Human IgG was adsorbed on the substrate of the device by the antigen-antibody reaction between Fab and human IgG on the substrate. The interference color of the substrate of the device turned violet (glancing angle 60 to 70 degrees). By treating the device with gold colloid, the change in interference color could be clearly determined visually at a glancing angle of 0 to 30 degrees.

EXAMPLE 26

An N,N'-dimethylformamide solution (0.1 ml) of S-acetylmercaptosuccinic anhydride (60 mg/ml) was added to 5 ml of a solution of human IgG in sodium phosphate buffer (0.1M, pH 6.5) in a concentration of 10 mg/ml, and they were reacted at 28° C. for 45 minutes. The solution was purified by gel column chromatography to give human IgG having 10 thiol groups per molecule of IgG.

A substrate of a device having a meleimide group prepared in the same way as in Example 25 was immersed in the thiol group-containing human IgG solution ($8.0 \times 10^{-2}$ mg/ml) at 4° C. for 12 hours. As a result of this immersion, the interference color of the substrate changed from orange to red. This showed that the thiol group-containing human IgG was fixed to the substrate. Then, when the substrate was further immersed for 30 minutes in a sheep anti-human IgG solution, the sheep anti-human IgG was adsorbed on the substrate by the antigen-antibody reaction between human IgG and sheep anti-human IgG, and the interference color of the substrate became violet (glancing angle: 60 to 70 degrees). By treating the device with gold colloid, the change of color could be clearly determined at a glancing angle of 0 to 30 degrees.

EXAMPLE 27

A stainless steel plate (mirror-surface finished) having a silicon dioxide layer with a thickness of 1000 Å was subjected to refluxing treatment in a 5% toluene solution of a compound of the following formula.

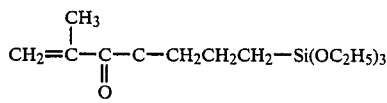

The substrate was immersed for 12 hours at 4° C. in a solution of Fab of sheep anti-human IgG ($4.8 \times 10^{-2}$ mg/ml), and further in a solution of human IgG ($5 \times 10^{-3}$ mg/ml), and subjected to gold colloid treatment as in Example 25. The human IgG could be detected with good visual determinability at a glancing angle of 0 to 30 degrees.

EXAMPLE 28

A stainless steel plate (mirror-surface finished) having a silicon dioxide layer with a thickness of 1000 Å was subjected to refluxing treatment in a 5% toluene solution of a compound of the following formula.

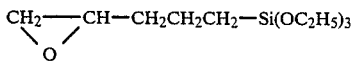

The substrate was immersed for 12 hours at 4° C. in an aqueous solution of anti-human IgG ($5 \times 10^{-2}$ mg/ml) and further in a solution of human IgG ($5 \times 10^{-3}$ mg/ml) for 30 minutes, and subjected to gold colloid treatment. At a glancing angle of 0 to 30 degrees, the portion where only the antibody was fixed and the portion of the antigenantibody reaction could be clearly distinguished visually a deep and light shades of violet.

COMPARATIVE EXAMPLE 2

A chrome-plated stainless steel substrate without an interference layer was immersed for 15 hours in an aqueous solution of human IgG ($5 \times 10^{-3}$ mg/ml), and then for 2 hours in an aqueous solution of anti-human IgG ($5 \times 10^{-2}$ mg/ml). The resulting detection structure was immersed for 2 hours in a gold colloid solution as in Examle 1. But no interference color was observed, and the site of the antigen-antibody reaction could not be distinguished either by visual inspection or by means of a color difference photometer.

EXAMPLE 29

The surface of the substrate having an $SiO_2$ layer formed thereon by sputtering, which had been prepared in Example 1 was immersed for 2 hours in a $1 \times 10^{-2}$ wt. % chloroform solution of octadecyltrichlorosilane to hydrophobize the surface of the $SiO_2$ layer.

Two such hydrophobized devices were immersed for 12 hours in an aqueous solution of human IgG ($5 \times 10^{-5}$M) to fix human IgG to the surface of the substrate. One of the human IgG-fixed devices was kept in contact with a $3 \times 10^7$M polystyrene latex having anti-human-IgG chemically fixed to its surface and an assay solution containing $2 \times 10^{-9}$M human IgG for 30 minutes.

For comparison, the other device was immersed in an aqueous solution containing $3 \times 10^{-7}$M polystyrene latex. The two devices were each treated with a gold colloid solution, and then compared with each other in the interference color of the surface.

The device immersed in the assay solution not containing the human IgG showed an interference color of blue violet, whereas the surface of e device immersed in the assay solution containing human IgG showed an interference color of pale blue, indicating a clear difference.

What is claimed is:

1. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), and a layer (III) of a substance for detecting said biological component provided at least in a region on the layer (II), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; then forming a light-transmitting reflecting layer (IV) on its surface, wherein said layer (IV) is a layer of a metal; and thereafter detecting the color of light interference or the brightness of the reflected light on the surface of the device.

2. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), and a layer (III) of a substance for detecting said biological component provided at least in a region on the layer (II), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; further reacting another substance capable of reacting with another reaction site in the biological component to be detected after or while reacting the detecting substance with the biological component to subject the surface layer of the device to contrast enhancement treatment; then forming a light-transmitting reflecting layer (IV) on its surface, wherein said layer (IV) is a layer of a metal; and thereafter detecting the color of light interference or the brightness of the reflected light on the surface of the device.

3. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), a hydrophobizing agent layer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; then forming a light-transmitting reflecting layer (IV) on its surface, wherein said layer (IV) is a layer of a metal; and thereafter detecting the color of light interference or the brightness of the reflected light on the surface of the device.

4. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), a hydrophobizing agent layer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; further reacting another substance capable of reacting with another reaction site in the biological component to be detected after or while reacting the detecting substance with the biological component to subject the surface layer of the device to contrast enhancement treatment; then forming a light-transmitting reflecting layer (IV) on its surface, wherein said layer (IV) is a layer of a metal; and thereafter detecting the color of light interference or the brightness of the reflected light on the surface of the device.

5. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), a reactive interlayer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; then forming a light-transmitting reflecting layer (IV) on its surface, wherein said layer (IV) is a layer of a metal; and thereafter detecting the color of light interference or the brightness of the reflected light on the surface of the device.

6. A method for detecting a component of a biological system, which comprises providing a biological component detecting device composed of a light reflecting substrate (I), made of a metal or metal alloy itself or having a surface of a metal or metal alloy, and being substantially free from diffused reflection, a light interference layer (II) formed on the substrate (I), a reactive interlayer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III); contacting said device with a solution containing the biological component to be detected; further reacting another substance capable of reacting with another reaction site in the biological component to be detected after or while reacting the detecting substance with the biological component to subject the surface layer of the device to contrast enhancement treatment; then forming a light-transmitting reflecting layer (IV) on its surface, wherein said layer (IV) is a layer of a metal; and thereafter detecting the color of light interference or the brightness of the reflected light on the surface of the device.

7. The method of claim 2, 4 or 6 wherein the other substance used for the contrast enhancement treatment is a secondary antibody, an enzyme-labelled secondary antibody, a secondary antibody fixed to an emulsion, or a secondary antibody fixed to a latex.

8. The method of any one of claims 1 to 6 wherein the substance in the biological component detecting substance layer (III) is an antibody, and the biological component to be detected is an antigen.

9. The method of any one of claims 1 to 6 wherein the substance in the biological component detecting substance layer (III) is an antigen, and the biological component to be detected is an antibody.

10. The method of any one of claims 1 to 6 wherein the substance in the biological component detecting substance layer (III) and the biological component to be detected are the same antigen, and an antibody added to the solution containing an antigen to be detected reacts competitively with both antigens.

11. The method of any one of claims 1 to 6 wherein the light-transmitting reflecting layer (IV) is a layer of a metal formed by a colloidal particle coating method.

12. The method of claim 11 wherein the metal is gold.

13. The method of claim 11 wherein the light-transmitting reflecting layer (IV) is a layer of metal colloid particles coated at a pH which is up to 1.0 higher than the isoelectric point of the biological component to be detected and lower than, or more than 1.0 higher than, the isoelectric point of the biological component detecting substance.

14. The method of claim 13 wherein the metal is gold.

15. The method of any one of claims 1 to 6 wherein the light reflectivity of the substrate is high such that the reflection on the substrate is balanced on the reflection of the light-transmitting reflecting layer.

16. The method of any one of claims 1 to 6 wherein the light-transmitting reflecting layer (IV) is a layer of a metal formed by a physical vapor deposition method.

17. The method of claim 16 wherein the metal is gold.

18. The method of any one of claims 1 to 6 wherein the interference color is detected by a color difference value calculated in accordance with the equation $$\Delta E^*ab = \sqrt{(\Delta L^*)^2 + (\Delta a^*) + (\Delta b^*)^2}$$

wherein $L^* = 116 \left(\frac{Y}{Y_o}\right)^{\frac{1}{3}} - 16$, $$a^* = 500 \left[\left(\frac{X}{X_o}\right)^{\frac{1}{3}} - \left(\frac{Y}{Y_o}\right)^{\frac{1}{3}}\right],$$

$$b^* = 200 \left[\left(\frac{Y}{Y_o}\right)^{\frac{1}{3}} - \left(\frac{Z}{Z_o}\right)^{\frac{1}{3}}\right],$$

$X_o$, $Y_o$, and $Z_o$ are tristimulus values of an illuminating light source, and X, Y and Z are tristimulus values of the spectrum of the calorimetric standard observer stipulated by International Committee of Illumination (1931).

19. A kit for detection of a component of a biological system, comprising (I) a pack of a device for detecting the biological component composed of a light reflecting substrate (I), made of a metal or metal alloy itself or having a surface of a metal or metal alloy, and being substantially free from diffused reflection, a light interference layer (II) formed on the substrate (I), and a layer (III) of a substance for detecting said biological component provided at least in a region on the layer (II), wherein the light interference layer (a) does not have substantially reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III), and (2) a pack of a metal colloid, and optionally (3) a pack of a contrast enhancement agent.

20. A kit for detection of a component of a biological system, comprising (1) a pack of a device for detecting the biological component of a light reflecting substrate (I), made of a metal or metal alloy itself or having a surface of a metal or metal alloy, and being substantially free from diffused reflection, a light interference layer (II) formed on the substrate (I), a hydrophobizing agent layer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III), and (2) a pack of a metal colloid, and optionally (3) a pack of a contrast enhancement agent.

21. A kit for detection of a component of a biological system, comprising (1) a pack of a device for detecting the biological component composed of a light reflecting substrate (I), made of a metal or metal alloy itself or having a surface of a metal or metal alloy, and being substantially free from diffused reflection, a light interference layer (II) formed on the substrate (I), a reactive interlayer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III), and (2) a pack of a metal colloid, and optionally (3) a pack of a contrast enhancement agent.

22. A device for detecting a component of a biological system, comprising a light reflecting substrate (I), made of a metal or metal alloy itself or having a surface of a metal or metal alloy, and being substantially free from diffused reflection, a light interference layer (II) formed on the substrate (I), and a layer (III) of a substance for detecting said biological component provided at least in a region on the layer (II), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III).

23. A device for detecting a component of a biological system, comprising a light reflecting substrate (I), made of a metal or metal alloy itself or having a surface of a metal or metal alloy, and being substantially free from diffused reflection, a light interference layer (II) formed on the substrate (I), a hydrophobizing agent layer (P) formed on the layer (II), and a layer (III) of a substance for detecting said biological component provided at least in a region on the layer (P), wherein the light interference layer (a) does not have substantial reflecting characteristics to visible light, namely a wavelength of 300 to 800 nm, (b) has a thickness and refractive index controlled such that an increase in the thickness of the layer (III) appears as a change in interference color, and (c) has a surface with sufficient affinity for the layer (III).

24. A device for detecting a component of a biological system, comprising a light reflecting substrate (I), made of a metal or metal alloy itself or having a surface of a metal or metal alloy, and being substantially free from diffused reflection, a light interference layer (II) formed on the substrate (I), a reactive interlayer (P) formed on the layer (II), and a layer (III) of a substrate for detecting said biological component provided at least in a region on the layer (P), wherein the light interference layer (a) does not have substantial reflecting characteristics to visible light, namely a wavelength of 300 to 800nm, (b) has a thickness and refractive index controlled such that an increase in the thickness of the layer (III) appears as a change in interference color, and (c) has a surface with sufficient affinity for the layer (III).

25. The device of claim 22, 23 or 24 wherein the substance in the biological detecting substance layer (III) is an antibody.

26. The device of claim 22, 23 or 24 wherein the substance in the biological component detecting substance layer (III) is an antigen.

27. The device of claim 22, 23 or 24 wherein the light interference layer (II) is a layer of an inorganic substance, and the biological component detecting substance layer (III) is a layer of an antibody protein which is formed by forming a complex of the antibody protein with a substantially water-insoluble mono- or bimolecular film, and laminating it to the light interference layer whose surface is optionally subjected to a hydrophobizing treatment.

28. The device of claim 22, 23 or 24 wherein the light interference layer (II) is a layer of an inorganic substance, and the biological component detecting substance layer (III) is a layer of an antibody protein which is formed by spreading a monomolecular film of a long-chain fatty acid having 24 to 32 carbon atoms, a polyvalent metal salt thereof and/or an ester thereof, or a monomolecular film of a polyvalent metal salt of a long-chain fatty acid having 14 to 23 carbon atoms and/or an ester of said fatty acid on a water phase, contacting the film with a water-soluble antibody protein dissolved in the water phase to form an antibody protein-monomolecular film complex on the interface of the aqueous phase, and laminating it onto the light interference layer (II).

* * * * *

UNITED STATES PATENT AND TRADEMARK OFFICE
CERTIFICATE OF CORRECTION

PATENT NO. : 4,820,649
DATED : April 11, 1989
INVENTOR(S) : Takeyuki KAWAGUCHI et al.

It is certified that error appears in the above-identified patent and that said Letters Patent is hereby corrected as shown below:

In the heading of the Patent, insert:

--Foreign Application Priority Data

Sept. 22, 1986  [JP]  Japan .......... 61-222058

Apr. 20, 1987   [JP]  Japan .......... 62-95367   --.

Signed and Sealed this

Twelfth Day of December, 1989

Attest:

JEFFREY M. SAMUELS

Attesting Officer

Acting Commissioner of Patents and Trademarks